United States Patent [19]

Keogh

[11] Patent Number: 5,891,506

[45] Date of Patent: *Apr. 6, 1999

[54] OXIDATIVE METHOD FOR ATTACHMENT OF GLYCOPROTEINS OR GLYCOPEPTIDES TO SURFACES OF MEDICAL DEVICES

[75] Inventor: James R. Keogh, Maplewood, Minn.

[73] Assignee: Medtronic, Inc., Minneapolis, Minn.

[ * ] Notice: The term of this patent shall not extend beyond the expiration date of Pat. No. 5,728,420.

[21] Appl. No.: 984,922

[22] Filed: Dec. 4, 1997

Related U.S. Application Data

[63] Continuation-in-part of Ser. No. 694,535, Aug. 9, 1996, Pat. No. 5,728,420.

[51] Int. Cl.$^6$ .............................. B05D 3/10; A61L 27/00; A61L 33/00
[52] U.S. Cl. .................... 427/2.13; 424/130.1; 424/94.3; 427/2.12; 427/2.24; 427/2.25; 427/2.3; 427/2.31; 427/338; 435/174; 435/176; 435/181; 435/188; 523/112; 523/113
[58] Field of Search .................... 427/2.1, 2.11, 427/2.12, 2.13, 2.24, 2.3, 338, 2.25, 2.31; 523/112, 113; 424/130.1, 94.3, 158.1; 106/124.3; 436/532, 87; 435/68.1, 41, 188, 174, 176, 181

[56] References Cited

U.S. PATENT DOCUMENTS

| | | | |
|---|---|---|---|
| 3,826,678 | 7/1974 | Hoffman et al. | 117/81 |
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,053,048 | 10/1991 | Pinchuk | 623/1 |
| 5,057,313 | 10/1991 | Shih | 424/85.91 |
| 5,077,372 | 12/1991 | Hu et al. | 528/70 |
| 5,104,976 | 4/1992 | Casellas et al. | 530/391.9 |
| 5,258,501 | 11/1993 | Barbaric et al. | 530/395 |
| 5,274,119 | 12/1993 | Frazier et al. | 548/521 |
| 5,344,455 | 9/1994 | Keogh et al. | 623/11 |
| 5,362,852 | 11/1994 | Geoghegan | 530/345 |
| 5,443,953 | 8/1995 | Hansen et al. | 424/1.49 |
| 5,521,290 | 5/1996 | Sivam et al. | 530/391.5 |
| 5,532,352 | 7/1996 | Pliura et al. | 540/145 |
| 5,614,487 | 3/1997 | Battersby et al. | 514/2 |
| 5,672,638 | 9/1997 | Verhoeven et al. | 427/2.25 |
| 5,677,276 | 10/1997 | Dickerson et al. | 514/8 |
| 5,728,420 | 3/1998 | Keogh | 427/2.12 |
| 5,795,560 | 8/1998 | Reed | 424/1.49 |

OTHER PUBLICATIONS

R. G. Dickinson, et al., "A New Sensitive and Specific Test for the Detection of Aldehydes: Formation of 6–Mercapto–3–substituted–s–Traizolo[4,3–b]–s–Tetrazines," *Chem. Commun.*, 1719–1720 (1970) ( no month).

K.F. Geoghegan, et al., "Site–Directed Conjugation of Nonpeptide Groups to Peptides and Proteins via Periodate Oxidation of a 2–Amino Alcohol. Application to Modification at N–Terminal Serine," *Bioconjugate Chem.*, 3, 138–146 (1992) (no month).

A.S. Hoffman, et al., "Covalent Binding of Biomolecules to Radiation–Grafted Hydrogels on Inert Polymer Surfaces," *Trans. Am. Soc. Artif. Intern. Organs*, 18, 10–18 (1972) (no month).

S. Holmes, et al. "Covalent Binding of Biomolecules to Radiation–Grafted Hydrogels on Inert Polymer Surfaces," *Trans. Am. Soc. Artif. Intern. Organs*, 18, 0–18 (1972) (no month).

Y. Ito, et al., "Materials for Enhancing cell Adhesion by Immobilization of Cell–Adhesive Peptide," *Biomed. Mat. Res.*, 25, 1325–1337 (1991) (No month).

P.H. O'Farrell, "High Resolution Two–Dimensional Electrophoresis of Proteins," *J. Biol. Chem.*, 250, 4007–4021 (1975) May.

*Primary Examiner*—Diana Dudash
*Attorney, Agent, or Firm*—Thomas F. Woods; Harold R. Patton

[57] ABSTRACT

A method for making a medical device having at least one glycoprotein and/or glycopeptide immobilized on a substrate surface is provided. The method may include oxidizing 1,2 dihydroxy moieties with a periodate to form an aldehyde-functional material; combining the aldehyde-functional material with an amino-functional material to bond the two materials together through an imine moiety; and reacting the imine moiety with a reducing agent to form a secondary amine. Another method of the present invention may be employed to crosslink glycoproteins and/or glycopeptides immobilized on medical device surfaces. Additionally, one method of the present invention may be employed to crosslink glycoproteins and/or glycopeptides, thereby forming a crosslinked biomaterial or a crosslinked medical device coating.

63 Claims, No Drawings

OXIDATIVE METHOD FOR ATTACHMENT OF GLYCOPROTEINS OR GLYCOPEPTIDES TO SURFACES OF MEDICAL DEVICES

CROSS-REFERENCE TO RELATED APPLICATION

This application is a continuation in part of application Ser. No. 08/694,535 filed Aug. 9, 1996, now U.S. Pat. No. 5,728,420.

BACKGROUND OF THE INVENTION

For many years, a number of medical devices (e.g., pacemakers, vascular grafts, stents, heart valves, etc.) that contact bodily tissue or fluids of living persons or animals have been developed, manufactured and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation may diminish the useful lifetime of many devices.

Implantable medical devices also tend to serve as foci for infection of the body by a number of bacterial species. These device-associated infections are promoted by the tendency of these organisms to adhere to and colonize the surface of the device. Consequently, it has been of great interest to physicians and the medical industry to develop surfaces that are less prone in promoting the adverse biological reactions that typically accompany the implantation of a medical device.

One approach for minimizing undesirable biological reactions associated with medical devices is to attach various biomolecules to their surfaces for the attachment and growth of a cell layer which the body will accept. Biomolecules such as growth factors, cell attachment proteins and cell attachment peptides have been used for this purpose. In addition, biomolecules such as antithrombogenics, antiplatelets, anti-inflammatories, antimicrobials and the like have also been used to minimize adverse biomaterial-associated reactions.

A number of approaches have been suggested to attach such biomolecules. These approaches typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to biomaterial surfaces. For example, covalent attachment of biomolecules using water soluble carbodiimides is described by Hoffman et al., "Covalent Binding of Biomolecules to Radiation-Grafted Hydrogels on Inert Polymer Surfaces", *Trans. Am. Soc. Artif. Intern. Organs*, 18, 10–18 (1972); and Ito et al., "Materials for Enhancing Cell Adhesion by Immobilization of Cell-Adhesive Peptide", *J. of Biomed. Mat. Res.*, 25, 1325–1337 (1991).

One type of biomolecule which is often coupled to biomaterial surfaces with coupling molecules is protein. Proteins are polypeptides made up of amino acid residues. A protein comprising two or more polypeptide chains is an oligomeric protein. In general, established coupling procedures couple proteins to substrate surfaces through a protein's lysine amino acid residues which contain terminal amino groups. This method of binding has several inherent problems. For example, if a number of lysine residues are present on a protein's surface, multiple attachments may occur. Multiple attachment sites may lead to multiple conformations of the protein on the biomaterial surface. The lack of coupling specificity may disrupt or destroy the biological activity of the protein being coupled. In addition, coupling molecules may add instability to the biomaterial surface and increase the prospect for burial of the attached protein in the coupling layer. Coupling molecules may also create nonspecific and undesirable crosslinks between protein molecules, thereby destroying the biological properties of the protein or they may create bonds amongst surface functional sites, thereby inhibiting attachment. The use of coupling molecules may also decrease the specificity for attachment of the protein to the biomaterial surface, thereby losing conformational control over the attachment process.

SUMMARY OF THE INVENTION

The present invention provides an improved method for covalently attaching a biomolecule to substrate surface. Specifically, the present invention provides a method for making a medical device having a least one glycoprotein and/or glycopeptide immobilized on a biomaterial surface. The method includes the steps of: combining a periodate with a glycoprotein and/or glycopeptide comprising a 1,2 dihydroxy moiety (RCHOHCHOHR') to form an aldehyde-functional material (RCHO); combining the aldehyde-functional material with a material comprising a primary amine moiety (R"NH$_2$) to bond the two materials together through an imine moiety (R"N=CHR); and reacting the imine moiety with a reducing agent to form an immobilized glycoprotein and/or glycopeptide on a medical device biomaterial surface through a secondary amine linkage (R"NH—CH$_2$R).

A preferred method of the present invention comprises the steps of combining a periodate with a glycoprotein and/or glycopeptide comprising a 1,2 dihydroxy moiety to form an aldehyde-functional material in an aqueous solution having a pH of about 4–9 and a temperature of about 50° C.; combining the aldehyde-functional material with a biomaterial surface comprising a primary amine moiety to immobilize the glycoprotein and/or glycopeptide on the substrate surface through an imine moiety; and reacting the imine moiety with a reducing agent to form an immobilized glycoprotein and/or glycopeptide on the biomaterial surface through a secondary amine linkage.

Another method of the present invention may be employed to crosslink glycoproteins and/or glycopeptides, located in solution or on biomaterial surfaces, comprising both a 1,2 dihydroxy moiety and a primary amine moiety. This method includes the steps of: combining a periodate with the glycoprotein and/or glycopeptide to oxidize the 1,2 dihydroxy moiety to form an aldehyde moiety; allowing the aldehyde moiety to combine with the amine moiety forming an imine moiety; and reacting the imine moiety with a reducing agent to form a secondary amine and a crosslinked material. This crosslinked material may be employed as a biomaterial or as a biomaterial coating. In addition, such crosslinked material may be further modified to contain additional biomolecules. For example, aldehyde-containing biomolecules may be attached to residual amine moieties present in or on the surface of the crosslinked material. Alternatively, amine-containing biomolecules may be attached to residual aldehyde moieties present in or on the surface of crosslinked material. Furthermore, glycoproteins and/or glycopeptides coated onto a biomaterial surface may be crosslinked according to still another method of the present invention.

DETAILED DESCRIPTION OF THE INVENTION

As used in the specification and claims hereof, the following terms have the particular meanings and definitions set forth below.

I define the term "glycoprotein" appearing herein as a conjugated protein which contains at least one carbohydrate group. Thus, according to my definition, a typical glycoprotein contains one or more oligosaccharide units linked to either asparagine amino acid residues by N-glycosidic bonds or serine or threonine amino acid residues by O-glycosidic bonds. The saccharide unit directly bonded to asparagine is typically N-acetylglucosamine, whereas N-acetylgalactosamine tends to be the saccharide unit bonded to serine or threonine residues. Oligosaccharides bound to glycoproteins may contain a variety of carbohydrate units, and tend to be located at sites away from the biologically active site of the protein. Thus, oligosaccharide moieties of glycoproteins may typically be modified with little or no effect on the biological properties of the protein. The glycoproteins suitable for use in the present invention include at least one carbohydrate group which possesses two or more hydroxyl (—OH) groups located on adjacent carbon atoms. Two hydroxyl groups located on adjacent carbon atoms is referred to as a 1,2 dihydroxy moiety.

I define the term "glycopeptide" appearing herein as a conjugated peptide which contains at least one carbohydrate group. Thus, according to my definition, peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tetrapeptides and pentapeptides. When there are many amino acids joined together, the structure is termed a polypeptide. In general, polypeptides contain less than 100 amino acid residues and proteins contain 100 or more amino acid residues. The glycopeptides suitable for use in the present invention include at least one carbohydrate group which contains two or more hydroxyl (—OH) groups located on adjacent carbon atoms.

I define the term "glycoprotein and/or glycopeptide" appearing herein as meaning any one or more of a glycoprotein alone, a combination of different glycoproteins, a glycopeptide alone, a combination of different glycopeptides, or a combination of one or more glycoproteins with one or more glycopeptides.

I define the term "biomaterial" appearing herein as a material designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties required to function for the intended purpose; may be purified, fabricated and sterilized easily; will substantially maintain its physical properties and function during the time that it remains implanted in or in contact with the body. Biomaterials suitable for use in the present invention include an amine moiety. In addition, biomaterials may be fabricated by crosslinking glycoproteins and/or glycopeptides, comprising both a 1,2 dihydroxy moiety and a primary amine moiety, according to one method of the present invention.

I define the term "medical device" appearing herein as a device having surfaces that contact tissue, blood, or other bodily fluids in the course of their operation, which fluids are subsequently used in patients. This definition includes within its scope, for example, extracorporeal devices for use in surgery such as blood oxygenators, blood pumps, blood sensors, tubing used to carry blood and the like which contact blood which is then returned to the patient. The definition also includes within its scope endoprostheses implanted in blood contact in a human or animal body such as vascular grafts, stents, pacemaker leads, heart valves, and the like that are implanted in blood vessels or in the heart. The definition includes within its scope devices for temporary intravascular use such as catheters, guide wires, and the like which are placed into blood vessels or the heart for purposes of monitoring or repair The present invention has an object of solving a number of problems associated with the use of medical devices. The present invention includes within its scope an oxidative process for covalently attaching glycoproteins and/or glycopeptides to biomaterial surfaces for use in medical devices. The present invention further provides an oxidative method for fabricating crosslinked biomaterials or crosslinked biomaterial coatings comprising glycoproteins and/or glycopeptides.

Proteins and/or peptides that possess a carbohydrate bearing a 1,2 dihydroxy moiety are oxidizable with periodate, which may be provided as periodic acid or salts thereof, such as sodium periodate, potassium periodate, or other alkali metal periodates. Typically, a stoichiometric amount of periodate is used to oxidize the 1,2 dihydroxy moiety, although an excess could be used. Oxidation of such glycoproteins and/or glycopeptides forms reactive aldehyde moieties within the glycoprotein and/or glycopeptide.

The oxidation is carried out in an aqueous solution, preferably an aqueous buffered solution, at room temperature that does not destroy the biological properties of the glycoproteins and/or glycopeptides. Generally, buffers having a pH in a range of about 4–9 may be used, with a pH of about 6–8 desired for certain pH sensitive glycoproteins and/or glycopeptides. Generally, the oxidation is carried out at a temperature of about 0°–50° C., and preferably at a temperature of about 4°–37° C. Depending on the glycoproteins and/or glycopeptides, oxidation reactions may be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher temperatures generally require shorter treatment times. Time and temperature limitations of the present invention are generally governed by the biological stability of the glycoproteins and/or glycopeptides imparted by the oxidation process. Wide latitude may be employed in determining optimum conditions for a particular system. Such conditions may be determined readily by one skilled in the art by routine experimentation upon examination of the information presented herein.

Subsequent to oxidation, the reaction solution may be stored prior to attachment to a substrate at about 4° C. Typically, the storage stability of the reaction solution at a neutral pH or slightly acidic pH may extend between about one and about fourteen for 1–14 days and sometimes even months when stored in the dark.

The resultant aldehyde moieties interact with sites on a biomaterial surface for covalent attachment of the glycoproteins and/or glycopeptides. These biomaterial surface attachment sites comprise amine moieties, which react with aldehyde moieties forming imines. The substrate surface to which the glycoprotein is to be coupled should contain an adequate density of amine moieties for attaching the desired number of glycoproteins and/or glycopeptides.

Biomaterials of the present invention not containing amines on their surfaces may be aminated readily through a number of methods well known in the art. For example, amines may be provided by plasma treating materials with ammonia gas as found in Holmes and Schwartz, "Amination of Ultra-high Strength Polyethylene using Ammonia Plasma", *Composites Science and Technology* 38, 1–21 (1990). Alternatively, amines may be provided by grafting acrylamide to the substrate followed by chemical modification to introduce amine groups by methods well known to those skilled in the art, e.g., Hofmann rearrangement reaction. Polyvinyl amines or polyalkylimines may also be covalently attached to polyurethane surfaces according to the method taught by U.S. Pat. No. 4,521,564 to Solomone et al. Alternatively, for example, aminosilane may be attached to the surface as set forth in U.S. Pat. No. 5,053,048 to Pinchuk, a grafted acrylamide-containing polymer may be attached by radiation grafting as set forth in U.S. Pat. No. 3,826,678 to Hoffman et al., a grafted N-(3-aminopropyl) methacrylamide-containing polymer may be attached by ceric ion grafting as set forth in U.S. Pat. No. 5,344,455 to Keogh et al.

Typically, when a aldehyde moiety (RCHO) reacts with a primary amine moiety (R'NH2), an equilibrium is set up with the reaction product, which is a relatively unstable imine moiety (R'N═CHR). This coupling reaction may be carried out under the same conditions described above for the oxidation, which are designed to protect the glycoprotein and/or glycopeptide from damage. To stabilize the linkage between the glycoprotein and/or glycopeptide and the biomaterial surface, subsequent reductive alkylation of the imine moiety is carried out using reducing agents (i.e., stabilizing agents) such as, for example, sodium borohydride, sodium cyanoborohydride, and amine boranes, to form a secondary amine (R'NH—CH$_2$R). This reaction may also be carried out under the same conditions described above for the oxidation. Typically, however, the coupling and stabilizing reactions are carried out in a neutral or slightly basic solution and at a temperature of about 0°–50° C. Preferably, the pH is about 6–10, and the temperature is about 4°–37° C., for the coupling and stabilizing reactions. These reactions (coupling and stabilizing) may be allowed to proceed for just a few minutes or for many hours. Commonly, the reactions are complete (i.e., coupled and stabilized) within 24 hours.

Generally, glycoproteins used according to this invention may be, for example anticoagulant and antithrombotic proteins, clotting proteins, platelet proteins, anti-inflammatory proteins, antibodies, immunoglobulins, defense proteins, enzymes, hormones, growth factors, globular proteins, blood proteins, regulatory proteins, transport proteins, fibrous proteins, structural proteins, membrane proteins, cell attachment proteins, proteoglymays, toxins, antibiotics, and ligands. The glycoproteins may be found in nature or may be synthesized chemically. As long as the glycoprotein contains a 1,2 dihydroxy moiety, it may be attached to an aminated biomaterial surface by the method of the present invention. If the glycoprotein contains an amine moiety in addition to a 1,2 dihydroxy moiety, it may be crosslinked to form a material which may be used as a biomaterial or a biomaterial coating.

Generally, glycopeptides used according to this invention may be, for example anticoagulant and antithrombotic peptides, clotting peptides, platelet peptides, anti-inflammatory peptides, defense peptides, enzymes, hormones, growth factors, neurotransmitters, cytokines, blood peptides, regulatory peptides, fibrous peptides, structural peptides, transport peptides, membrane peptides, cell attachment peptides, proteoglymays, toxins, antibiotics, and ligands. The glycopeptides may be found in nature or may be synthesized chemically. As long as the glycopeptide contains a 1,2 dihydroxy moiety, it may be attached to an aminated biomaterial surface by the method of the present invention. If the glycopeptide contains an amine moiety in addition to a 1,2 dihydroxy moiety, it may be crosslinked to form a material which may be used as a biomaterial or a biomaterial coating.

Glycoproteins or glycopeptides, or a combination of glycoproteins and glycopeptides, may be chemically synthesized by a number of methods well known to those skilled in the art. Typically, methods for synthesizing proteins or peptides from amino acids are divided into two categories: solution (classical) synthesis methods and solid phase (e.g., SPPS) synthesis methods. Peptides of varying length may also be formed by the partial hydrolysis of very long polypeptide chains of proteins. Glycoproteins and/or glycopeptides may be formed from natural or chemical synthesized proteins and/or peptides by glycosylation, which is the addition of carbohydrate side chains.

There are a number of methods well known to those skilled in the art for glycosylating proteins or peptides. For example, side-chain glycosylation may be performed chemically with glycosylbromides for serine and threonine amino acid residues and glycosylamines for aspartic acid amino acid residues, thereby producing glycosylated asparagine amino acid residues. In addition, glycosylating enzymes may be used to attach carbohydrate side chains to proteins or peptides.

Some glycoproteins or glycopeptides are susceptible to conformational changes when brought into contact with a hydrophobic substrate surface. These conformational changes may lead to the exposure of internalized nonpolar groups which may lead to hydrophobic interactions between the glycoprotein and/or glycopeptide and the surface. These hydrophobic interactions may cause the exclusion of water molecules that normally surround the glycoprotein and/or glycopeptide in solution. This exclusion of water molecules between the protein or peptide and the surface strengthens the hydrophobic interaction and may cause further conformational change of the protein or peptide. The degree of conformational change a glycoprotein and/or glycopeptide experiences may or may not destroy its biological properties. Therefore, one must take into account the hydrophobic nature of the substrate surface when attaching glycoproteins and/or glycopeptides which are prone to hydrophobic interactions. In such cases, it is prefered to create a hydrophilic environment on the biomaterial surface, thereby preventing any unwanted hydrophobic interactions between the glycoprotein and/or glycopeptide and the surface which may destroy the biological properties of the protein or peptide.

There are a number of surface-derivatization techniques (e.g., grafting techniques) well known to those skilled in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

Substrates that may be modified according to one method of the present invention include metals such as titanium, titanium alloys, TiNi alloys, shape memory alloys, super elastic alloys, aluminum oxide, platinum, platinum alloys, stainless steel, stainless steel alloys, MP35N, elgiloy, haynes 25, stellite, pyrolytic carbon, silver or glassy carbon; polymers such as polyamides, polycarbonates, polyethers, polyesters, polyolefins including polyethylenes or polypropylenes, polystyrenes, polyurethanes, polyvinyl chlorides, polyvinylpyrrolidones, silicone elastomers, fluoropolymers, polyacrylates, polyisoprenes, polytetrafluoroethylenes, rubber, minerals or ceramics such as hydroxapatite; human or animal protein or tissue such as bone, skin, teeth, collagen, laminin, elastin or fibrin; organic materials such as wood, cellulose or compressed carbon, and other materials such as glass and the like. Biomaterials of the present invention made using these materials may be coated or uncoated, and derivatized or underivatized.

One method of the invention may be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lens for the eye such as contact or intraocular lenses, blood handling equipment, apheresis equipment, diagnostic and monitoring catheters and sensors, biosensors, dental devices, drug delivery systems, or bodily implants of any kind.

It will also be understood by one skilled in the art that glycoproteins or glycoprotein coatings as well as glycopeptides and/or glycopeptide coatings may be crosslinked using a method of the present invention. That is, glycoproteins and/or glycopeptides or glycoprotein and/or glycopeptide coatings that contain both primary amine moieties and 1,2 dihydroxy moeities may be crosslinked to provide desired physical and biological properties. The resultant imines formed following the crosslinking of the aldehydes (as a result of oxidation of the 1,2 dihydroxy moieties) and amines may be stabilized using a reducing agent as described above.

For example, structural glycoproteins and/or glycopeptides may be crosslinked to form a material that may be used as a biomaterial or a biomaterial coating. Also, additional glycoproteins and/or glycopeptides, as described herein, may be attached to residual amine moieties contained in or on a fabricated crosslinked glycoprotein and/or glycopeptide biomaterial or biomaterial coating, as described herein. Alternatively, amine containing biomolecules may be attached to residual aldehyde moieties contained in or on a fabricated crosslinked glycoprotein and/or glycopeptide biomaterial or biomaterial coating, as described herein.

An example of a glycoprotein of the present invention is fibrin(ogen). Fibrin(ogen), which is a structural protein, has oligosaccharides which may be oxidized with a source of periodate, which may be provided as periodic acid or salts thereof, such as sodium periodate, potassium periodate, or other alkali metal periodates, to form a pendant aldehyde moiety. The resultant aldehyde moieties may be used to crosslink the fibrin(ogen) through bonds formed between the aldehydes and amines (lysine amino acid residues) contained on neighboring fibrin(ogen) molecules. The resultant imine bonds may then be reduced using a mild reducing agent like sodium borohydride, sodium cyanoborohydride, or amine boranes. These crosslinks may endow the fibrinogen and/or fibrin (thrombin polymerized fibrinogen) biomaterial or biomaterial coating with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the fibrinogen and/or fibrin to control its physical and biological properties.

The aldehyde moieties formed by oxidation of fibrin (ogen) may also be used to couple a variety of amine-containing biomolecules to the crosslinked fibrin(ogen) biomaterial or biomaterial coating. Also, the ability to create aldehyde moieties along fibrin(ogen) molecules enables them to be covalently attached to amine containing biomaterial surfaces. Such fibrinogen/fibrin coated biomaterial surfaces may be used, for example, as cell seeding surfaces, cell binding surfaces, cell separating surfaces, fibrinogen/fibrin-coated stents, fibrinogen/fibrin-coated vascular grafts or fibrinogen/fibrin glues.

Although the examples described below relate generally to treatment of polymeric films or tissue culture plates as substrate surfaces, those examples are merely illustratative and are intended to limit in no way the scope of the present invention.

EXAMPLE 1

Periodate Oxidation of Bovine Fibrinogen

A glycoprotein bovine fibrinogen obtained from Sigma Chemical Co. (St. Louis, Mo.) was incubated in sodium metaperiodate ($NaIO_4$) also obtained from Sigma Chemical Co. (St. Louis, Mo.). The following four fibrinogen solutions were prepared to investigate the oxidation of fibrinogen with varying amounts of periodate: (1) 0.03 mM fibrinogen, 0.2 mM $NaIO_4$, 0.008M $Na_2HPO_4$, 0.002M $KH_2PO_4$, 0.14M NaCl, pH 7.4; (2) 0.03 mM fibrinogen, 0.1 mM $NaIO_4$, 0.008M $Na_2HPO_4$, 0.002M $KH_2PO_4$, 0.14M NaCl, pH 7.4; (3) 0.03 mM fibrinogen, 0.05 mM $NaIO_4$, 0.008M $Na_2HPO_4$, 0.002M $KH_2PO_4$, 0.14M NaCl, pH 7.4; and (4) 0.03 mM fibrinogen, 0.008M $Na_2HPO_4$, 0.002M $KH_2PO_4$, 0.14M NaCl, pH 7.4.

The four fibrinogen solutions were incubated in the dark for 2 hours while shaking at room temperature. The resultant solutions, 500 µl of each, were added to 2 ml of a solution containing 0.8 g NaOH, 0.2 g 4-amino-3-hydrazino-5-mercato-1,2,4-triazole, which is available under the trade designation PURPALD from Sigma Chemical Co. (St. Louis, Mo.), in 20 ml deionized water, and shaken vigorously for 15 minutes at room temperature. Dickinson and Jacobsen, *Cem. Commun.*, 1719 (1970), described the specific and sensitive reaction of aldehydes with PURPALD to yield purple-to-magenta-colored 6-mercapto-s-triazolo-(4, 3-b)-s-tetrazines.

After 15 minutes of shaking at room temperature, the resultant solutions were analyzed spectrophotometrically at 550 nm. Sample 4 was used as the blank. Sample absorbances obtained at 550 nm were 0.54 for sample 1, 0.53 for sample 2 and 0.51 for sample 3, indicating that for all samples the fibrinogen was successfully oxidized to form aldehyde groups.

EXAMPLE 2

Periodate Oxidation of Bovine Vitronectin

A glycoprotein bovine vitronectin obtained from Sigma Chemical Co. (St. Louis, Mo.) was incubated in sodium metaperiodate ($NaIO_4$) also obtained from Sigma Chemical Co. (St. Louis, Mo.). The following two vitronectin solutions were prepared: (1) 0.001 mM vitronectin, 0.05M $NaIO_4$ and (2) 0.001 mM vitronectin. Both solutions were incubated in the dark for 2 hours while shaking at room temperature. The resultant solutions, 100 µl of each, were added to 2 ml PURPALD solution described in Example 1, and shaken vigorously for 30 minutes at room temperature.

After 30 minutes of shaking at room temperature, the resultant solutions were analyzed spectrophotometrically at 550 nm. The PURPALD solution was used as the blank. Sample absorbances obtained at 550 nm were 0.09 for sample 1 and 0.04 for sample 2, indicating that vitronectin was successfully oxidized to form aldehyde groups.

EXAMPLE 3

Periodate Oxidation of Bovine Fibronectin

A glycoprotein bovine fibronectin obtained from Sigma Chemical Co. (St. Louis, Mo.) was incubated in sodium metaperiodate ($NaIO_4$) also obtained from Sigma Chemical Co. (St. Louis, Mo.). The following two fibronectin solutions were prepared: (1) 0.002 mM fibronectin, 0.05M $NaIO_4$, 0.5M NaCl, 0.05M Tris, pH 7.5; and (2) 0.002 mM fibronectin, 0.5M NaCl, 0.05M Tris, pH 7.5. Both solutions were incubated in the dark for 2 hours while shaking at room temperature. The resultant solutions, 100 µl of each, were added to 2 ml PURPALD solution describe in Example 1 and shaken vigorously for 30 minutes at room temperature.

After 30 minutes of shaking at room temperature, the resultant solutions were analyzed spectrophotometrically at 550 nm. Following an initial analysis, sample 1 was observed to contain too many aldehydes to measure accurately. Therefore, sample 1 was diluted 1:50 in deionized water to provide a solution containing a measurable amount of aldehydes. The PURPALD solution was used as the blank. Sample absorbances obtained at 550 nm were 0.81 for sample 1 and 0.0 for sample 2, indicating that the fibronectin in sample 1 was successfully oxidized forming aldehyde groups. Fibronectin in sample 2 was not oxidized due to the omission of periodate.

EXAMPLE 4

Attachment of Fibronectin to Aminated Substrates

A fibronectin was covalently attached to a substrate surface. The attachment technique began with the graft copolymerization of acrylamide (AAm) and N-(3-aminopropyl)methacrylamide (APMA) monomers onto an ozone treated polystyrene tissue culture plate with ceric ($Ce^{IV}$) ions. The $Ce^{IV}$ ions created free radicals on the ozone treated surface which initiated the graft copolymerization of the acrylamides. The amount of surface amination (the graft copolymerization of APMA and AAm) that took place on the substrate surface was measured via staining with ponceau S dye, a negatively charged dye molecule. Following grafting, fibronectin was coupled to the amine containing derivatized substrate surface. Fibronectin was first oxidized with sodium metaperiodate ($NaIO_4$) forming reactive aldehyde groups. These aldehyde groups were then used to covalently attached fibronectin to the primary amino groups present on the substrate surface. Sodium cyanoborohydride ($NaCNBH_3$) was then used to stabilize the imine linkages. The specific procedures for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposes the flowing oxygen to an 8000 V electrical potential. Following ozone treatment, the plates were soaked in nitrogen purged deionized water for 30 minutes at room temperature. Following the 30 minute soak in nitrogen purged deionized water, the plates were grafted with acrylamide (AAm) and N-(3-aminopropyl)methacrylamide (APMA) monomers (from Eastman Kodak Co., Rochester, N.Y.) using ammonium cerium (IV) nitrate (from Aldrich Chemical Co., Milwaukee, Wis.). The grafting solution consisted of 11.2M AAm, 1.1M APMA, 400 mM nitric acid and 40 mM ammonium cerium (IV) nitrate in deionized water.

The plates were allowed to graft for 3 hours in a 65° C. nitrogen purged oven. Following grafting the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. The results demonstrated that the surface-derivatized plates contained primary amines on their surfaces.

Bovine fibronectin obtained from Sigma Chemical Co. (St. Louis, Mo.) was then incubated in sodium metaperiodate ($NaIO_4$) also obtained from Sigma Chemical Co. (St. Louis, Mo.). The following fibronectin solution was prepared: 0.002 mM fibronectin, 0.05M $NaIO_4$, 0.5M NaCl, 0.05M Tris, pH 7.5. The solution was incubated in the dark for 2 hours while shaking at room temperature. Sodium cyanoborohydride (1 mg/ml) was then added to the fibronectin solution. The resultant solution was immediately added to each of the amine containing surface-derivatized tissue culture plate wells (approximately 1 ml solution/well). The fibronectin solution incubated in the derivatized tissue culture plate wells overnight at room temperature.

Following incubation, the wells were then vigorously rinsed with phosphate buffered saline (PBS) solution. The attachment of fibronectin to the amine containing surface-derivatized tissue culture plate surfaces was assessed using toluidine blue dye, a positively charged dye molecule. This dye ionically associates with the negative charges on a substrate surface. Therefore, any binding of toluidine blue dye to a fibronectin-derivatized surface is caused by the presence of negative charges in the fibronectin.

The wells of each plate were filled with a 1% toluidine blue dye in deionized water solution. After about a 5 minute incubation at room temperature, the dye solution was removed and the wells were thoroughly rinsed with PBS. The surface associated dye in each well was then eluted by mechanically shaking the plates in a 1% SDS in deionized water solution overnight. The amount of dye eluted from the wells was then determined spectrophotometrically at 630 nm. Sample absorbances obtained at 630 nm were 0.05 for the nonderivatized sample plate, 0.54 for the AAm/APMA-derivatized sample plate and 1.83 for the fibronectin-derivatized sample plate, indicating that the fibronectin was successfully oxidized and then covalently attached to the substrate surface.

EXAMPLE 5

ELISA and Cellular Adherence to Fibronectin Coupled Surfaces

A polyurethane in the form of Pellethane 2363-55D was obtained from Dow Chemical Co. (Midland, Mich.) and extruded in a film. The film was cut into 1 cm sample disks. Sample disks were then cleansed with ethanol and surface grafted with AAm and APMA monomers using $Ce^{IV}$ ion. The grafting solution comprised 11.2M AAm, 1.1M APMA, 400 mM nitric acid and 40 mM ammonium cerium (IV) nitrate in deionized water. The sample disks were placed into the grafting solution and allowed to graft for 1 hour at room temperature. Following grafting, the sample disks were thoroughly washed with deionized water. Fibronectin was then coupled to the resultant APMA/Am surface-derivatized sample disks via two methods.

A first method included oxidizing fibronectin with sodium metaperiodate. Fibronectin (0.1 mg/ml) was exposed in the dark to a 1 µg/ml sodium metaperiodate in deionized water solution for 3 hours at room temperature. The APMA/Am-derivatized sample disks were then placed into the oxidized fibronectin solution for 24 hours at room temperature. Sample disks were then thoroughly rinsed with deionized water. The samples were then incubated for 24 hours at room temperature in a 3 mg/ml sodium cyanoborohydride in deionized water solution. Sample disks were then thoroughly rinsed with deionized water.

A second method included employing glutaraldehyde as a coupling agent. The second method included soaking the APMA/Am-derivatized sample disks in a 2% glutaraldehyde in deionized water solution for 2 hours at room temperature. Sample disks were then thoroughly rinsed with deionized water. Following rinsing, the sample disks were then incubated in a 0.1 mg/ml fibronectin in deionized water solution for 24 hours at room temperature. Sample disks were then thoroughly rinsed with deionized water. The sample disks were then incubated for 24 hours at room temperature in a 3 mg/ml sodium cyanoborohydride in deionized water solution. Sample disks were then thoroughly rinsed with deionized water.

An enzyme linked immunosorbent assay (ELISA) was then performed to determine the ability of an antibody to recognize the fibronectin which had been coupled to the sample surfaces. Sample disks were washed for 20 minutes at room temperature with wash buffer (pH 7.4) consisting of 10 mM Tris, 0.15M NaCl and 0.05% Tween. Sample disks were then incubated at 37° C. for 30 minutes in blocking buffer (pH 7.4) consisting of 10 mM Tris, 0.15M NaCl, 0.05% Tween and 0.05% gelatin followed by three 10 minute washes with wash buffer. Next, sample disks were incubated at 37° C. for 1 hour in a primary antibody solution (pH 7.4) consisting of 10 mM Tris, 0.15M NaCl and 2 µg/ml mouse monoclonal anti-fibronectin antibody (Sigma Chemical Co., St. Louis, Mo.). Sample disks were then rinsed thrice (10 minutes per wash) with wash buffer. Sample disks were then incubated at 37° C. for 1 hour in a peroxidase-labeled secondary antibody solution (pH 7.4) consisting of 10 mM Tris, 0.15M NaCl and 0.5 ng/ml anti-mouse IgG peroxidase antibody conjugate (Sigma Chemical Co., St. Louis, Mo.), followed by rinsing the sample disks thrice (10 minutes per wash) with wash buffer.

Sample disks were then incubated for 15 minutes at room temperature in a phosphate-citrate buffer (pH 5.0) containing 0.4 mg/ml o-phenyldiamine dihydrochloride and 0.2 µl/ml 30% hydrogen peroxide. The phosphate-citrate buffer consisted of 50 mM dibasic sodium phosphate and 25 mM citric acid in deionized water. Following the 15 minute incubation, the peroxide reaction was stopped with 3M HCl and the absorbance of the resultant solution was measured spectrophotometrically at 492 nm. The APMA/AAm-derivatized sample disks were used as controls for this experiment. Sample absorbances obtained from the spectrophotometric analysis were 0.016±0.038 for APMA/AAm-derivatized samples which contained glutaraldehyde coupled fibronectin and 0.204±0.068 for APMA/Am-derivatized samples which contained periodate oxidized fibronectin. The results indicated that the periodate oxidation method was more successful in attaching fibronectin to sample surfaces.

A cellular adherence assay was also performed to determine the ability of cells to adhere to fibronectin-derivatized sample surfaces. sample disks were incubated for 1 hour at 37° C. in a blocking buffer consisting of 2 mg/ml ovalbumin in phosphate buffered saline (PBS), pH 7.4. Mouse fibroblasts (C3T3) obtained from Amerimay Type Culture Collection (Rockville, Md.) and maintained in Dulbecco's modified Eagle's medium (DMEM) supplemented with 10% fetal bovine serum were harvested using trypsin:EDTA and resuspended in serum-free DMEM containing 2 mg/ml ovalbumin. The cells were then washed twice, counted and resuspended to a final density of $5 \times 10^4$ cells/ml in serum-free DMEM containing 2 mg/ml ovalbumin. Sample disks were then incubated in the cell suspension for 1 hour at 37° C. Nonadherent cells were removed by a PBS wash. Sample disks were fixed in 3% paraformaldehyde solution for 30 minutes. Adherent cells were then stained with a staining solution consisting of 1% toluidine blue dye and 3% paraformaldehyde in PBS. Following staining, sample surfaces were then examined for cellular adherence using a light microscope. Upon examination, APMA/AAm-derivatized samples and APMA/AAm-derivatized samples which contained glutaraldehyde coupled fibronectin appeared to have no adherent cells. In contrast, cells did appear to adhere to APMA/AAm-derivatized samples which contained periodate oxidized fibronectin.

EXAMPLE 6

Crosslinking of Fibrinogen

A porcine fibrinogen obtained from Sigma Chemical Co. (St. Louis, Mo.) was incubated in sodium metaperiodate ($NaIO_4$) also obtained from Sigma Chemical Co. (St. Louis, Mo.) and sodium cyanoborohydride ($NaCNBH_3$) obtained from Aldrich Chemical Co. (Milwaukee, Wis.). The following fibrinogen solution was prepared: 0.03 mM fibrinogen, 0.02M $NaIO_4$, 0.02M $NaCNBH_3$, 0.008M $Na_2HPO_4$, 0.002M $KH_2PO_4$, 0.14M NaCl, pH 7.4. The solution was then shaken vigorously and placed into a 24 well tissue culture plate (approximately 1 ml of fibrinogen solution/well).

The plate was then incubated in the dark for 2 hours while shaking at room temperature. After 2 hours, the solution was observed to have become cloudy and very viscous indicating the fibrinogen had crosslinked. The sample was then shaken for an additional 22 hours in the dark. Following incubation, the crosslinked fibrinogen was tested for residual aldehydes using the PURPALD solution describe in Example 1. The results of the PURPALD assay demonstrated few residual aldehydes were present which indicated the formation of covalent crosslinks between the aldehydes and the amines present along the fibrinogen molecules.

The following bovine fibrinogen (obtained from Sigma Chemical Co., St. Louis, Mo.) solution was prepared: 0.02 mM fibrinogen, 0.008M $Na_2HPO_4$, 0.002M $KH_2PO_4$, 0.14M NaCl, pH 7.4. Following preparation, the solution was divided into four equal portions. Sodium metaperiodate (0.05 mM) was then added to samples 3 and 4. All four fibrinogen solutions were then incubated in the dark for 2 hours while shaking at room temperature. Next, 0.02 mM NaCNBH$_3$ was added to samples 2 and 4. Again, all four fibrinogen solutions were allowed to react for 2 hours while shaking at room temperature. The samples, 50 μl of each, were then placed into 450 μl of SDS-PAGE buffer solution consisting of 62.5 mM Tris-HCL, 5% b-mercaptoethanol, 10% glycerol and 2.3% SDS. Samples were then boiled for 3 minutes. The samples, 10 μl of each, were then loaded onto a 4–15% gradient gel and SDS-PAGE was performed according to the procedures described in O'Farrell, "High Resolution Two-dimensional Electrophoresis of Proteins", *J. Biol. Chem.* 250, 4007–4021 (1974).

Following electrophoresis, the gel was stained with Coomassie Brilliant Blue, and the identity of the eluted proteins was determined by reference to molecular weight standards included on the gel. The results from SDS-PAGE indicated that the fibrinogen molecules in sample 4 had formed stable covalent crosslinks. In contrast, the results demonstrated that the fibrinogen molecules in the samples which contained no NaIO$_4$ had formed no crosslinks.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

I claim:

1. A method of forming a coating on a surface of a medical device, the coating imparting improved biocompatibility characteristics to the surface, the surface being suitable for contacting tissue, blood and other bodily fluids in or temporarily removed from a living mammalian subject, the method comprising the ordered steps of:

(a) combining a periodate with a biomolecule, the biomolecule comprising a 1,2 dihydroxy moiety and an amino acid residue for oxidizing the 1,2 dihydroxy moiety to form an aldehyde-functional material;

(b) providing the medical device, the device having a suitable biomaterial forming the surface, an amine moiety being disposed on the surface;

(c) combining the aldehyde-functional material with the amine moiety to bond the aldehyde-functional material to the amine moiety and thereby form an imine moiety; and (d) reacting the imine moiety with a reducing agent to form an amine linkage, the amine linkage immobilizing the biomolecule on the surface, the immobilized biomolecule forming the coating.

2. The method of claim 1, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

3. The method of claim 1, wherein the biomolecule is selected from the group consisting of a glycoprotein and a glycopeptide.

4. The method of claim 3, wherein the glycoprotein is selected from the group consisting of an anticoagulant protein, an antithrombotic protein, a clotting protein, a platelet protein, an anti-inflammatory protein, an antibody, an immunoglobulin, a defense protein, an enzyme, a hormone, a growth factor, a globular protein, a blood protein, a regulatory protein, a transport protein, a fibrous protein, a structural protein, a membrane protein, a cell attachment protein, a proteoglycan, a toxin, and a ligand.

5. The method of claim 3, wherein the glycoprotein is a naturally occurring glycoprotein.

6. The method of claim 3, wherein the glycoprotein is synthesized chemically.

7. The method of claim 3, wherein the glycopeptide is selected from the group consisting of an anticoagulant peptide, an antithrombotic peptide, a clotting peptide, a platelet peptide, an anti-inflammatory peptide, a defense peptide, an enzyme, a hormone, a growth factor, a neurotransmitter, a cytokine, a blood peptide, a regulatory peptide, a transport peptide, a fibrous peptide, a structural peptide, a membrane peptide, a cell attachment peptide, a toxin, an antibiotic, and a ligand.

8. The method of claim 3, wherein the glycopeptide is a naturally occurring glycopeptide.

9. The method of claim 3, wherein the glycopeptide is synthesized chemically.

10. The method of claim 1, wherein the periodate comprises at least one of periodic acid, sodium periodate, alkali metal periodates, and potassium periodate.

11. The method of claim 1, wherein the periodate is combined with the 1,2 dihydroxy moiety in an aqueous solution having a pH between about 4 and about 9.

12. The method of claim 1, wherein the periodate is combined with the 1,2 dihydroxy moiety in an aqueous solution having a temperature between about 0 and about 50 degrees Celsius.

13. The method of claim 1, wherein the aldehyde-functional material and the amine-functional material are combined in an aqueous solution having a pH between about 6 and about 10.

14. The method of claim 1, wherein the aldehyde-functional material and the amine-functional material are combined in an aqueous solution having a temperature between about 0 and about 50 degrees Celsius.

15. The method of claim 1, wherein the reducing agent comprises at least one of sodium borohydride, sodium cyanoborohydride, and amine borane.

16. The method of claim 1, wherein the reducing agent is combined with the imine moiety in an aqueous solution having a pH between about 6 and about 10.

17. The method of claim 1, wherein the reducing agent is combined with the imine moiety in an aqueous solution having a temperature between about 0 and about 50 degrees Celsius.

18. The method of claim 1, wherein the oxidizing step is performed in the absence of light.

19. The method of claim 1, wherein at least a portion of the surface forms at least one of a tube, a rod, a membrane, a balloon, a bag and a sheet.

20. The method of claim 1, wherein the surface comprises at least one of a biocompatible material selected from the group consisting of metal, titanium, titanium alloys, tin-nickel alloys, shape memory alloys, aluminum oxide, platinum, platinum alloys, stainless steel, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

21. A method of crosslinking a coating on a surface of a medical device, the coating imparting improved biocompatibility characteristics to the surface, the surface being suitable for contacting tissue, blood and other bodily fluids in or temporarily removed from a living mammalian subject, the method comprising the ordered steps of:

(a) immobilizing a biomolecule on the surface, the biomolecule forming the coating and comprising a 1,2 dihydroxy moiety, an amino acid residue and an amine moiety;

(b) applying a periodate to the coating to oxidize the 1,2 dihydroxy moiety to form an aldehyde moiety;

(c) allowing the aldehyde moiety to combine with the amine moiety to form an imine moiety; and (d) reacting the imine moiety with a reducing agent to form a secondary amine and thereby cause at least portions of the coating to crosslink.

22. The method of claim 21, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

23. The method of claim 21, wherein the biomolecule is selected from the group consisting of a glycoprotein and a glycopeptide.

24. The method of claim 23, wherein the glycoprotein is selected from the group consisting of an anticoagulant protein, an antithrombotic protein, a clotting protein, a platelet protein, an anti-inflammatory protein, an antibody, an immunoglobulin, a defense protein, an enzyme, a hormone, a growth factor, a globular protein, a blood protein, a regulatory protein, a transport protein, a fibrous protein, a structural protein, a membrane protein, a cell attachment protein, a proteoglycan, a toxin, and a ligand.

25. The method of claim 23, wherein the glycoprotein is a naturally occurring glycoprotein.

26. The method of claim 23, wherein the glycoprotein is synthesized chemically.

27. The method of claim 23, wherein the glycopeptide is selected from the group consisting of an anticoagulant peptide, an antithrombotic peptide, a clotting peptide, a platelet peptide, an anti-inflammatory peptide, a defense peptide, an enzyme, a hormone, a growth factor, a neurotransmitter, a cytokine, a blood peptide, a regulatory peptide, a transport peptide, a fibrous peptide, a structural peptide, a membrane peptide, a cell attachment peptide, a toxin, an antibiotic, and a ligand.

28. The method of claim 23, wherein the glycopeptide is a naturally occurring glycopeptide.

29. The method of claim 23, wherein the glycopeptide is synthesized chemically.

30. The method of claim 21, wherein the periodate comprises at least one of periodic acid, sodium periodate, alkali metal periodates, and potassium periodate.

31. The method of claim 21, wherein the reducing agent comprises at least one of sodium borohydride, sodium cyanoborohydride, and amine borane.

32. The method of claim 21, wherein the periodate is combined with 1,2 dihydroxy moiety and the amine moiety in an aqueous solution having a pH between about 4 and about 9.

33. The method of claim 21, wherein the periodate is combined with the 1,2 dihydroxy moiety and the amine moiety in an aqueous solution having a temperature between about 0 and about 50 degrees Celsius.

34. The method of claim 21, wherein the reducing agent is combined with the material comprising an imine moiety in an aqueous solution having a pH between about 6 and about 10.

35. The method of claim 21, wherein the reducing agent is combined with the imine moiety in an aqueous solution having a temperature between about 0 and about 50 degrees Celsius.

36. The method of claim 21, wherein the oxidizing step is performed in the absence of light.

37. The method of claim 21, wherein at least a portion of the surface forms at least one of a tube, a rod, a membrane, a balloon, a bag and a sheet.

38. The method of claim 21, wherein the surface comprises a biocompatible material selected from the group consisting of metal, titanium, titanium alloys, tin-nickel alloys, shape memory alloys, aluminum oxide, platinum, platinum alloys, stainless steel, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

39. A method of forming an insoluble crosslinked biomaterial for use in a medical device, the biomaterial being suitable for contacting tissue, blood and other bodily fluids in or temporarily removed from a living mammalian subject, the method comprising the ordered steps of:

(a) combining a periodate with at least two different cross-linking biomolecules, each biomolecule comprising a 1,2 dihydroxy moiety, an amino acid residue, and an amine moiety, the periodate oxidizing the 1,2 dihydroxy moiety to form an aldehyde moiety;

(b) allowing the aldehyde moiety of one biomolecule to combine with the amine moiety of another biomolecule to form an imine moiety; and (c) reacting the imine moiety with a reducing agent to form a secondary amine and thereby forming an insoluble crosslinked biomaterial.

40. The method of claim 39, wherein the medical device is selected from the group consisting of a blood-contacting medical device, a tissue-contacting medical device, a bodily fluid-contacting medical device, an implantable medical device, an endoprosthesis medical device, a cell seeding medical device, a cell binding medical device, a cell separating medical device, a vascular graft, a heart valve, and a tissue glue.

41. The method of claim 39, comprising the further step of forming the crosslinked biomaterial into at least one shape selected from the group consisting of a tube, a rod, a membrane, a balloon and a bag.

42. The method of claim 39, wherein at least one of the at least two different biomolecules is selected from the group consisting of a glycoprotein and a glycopeptide.

43. The method of claim 42, wherein the glycoprotein is selected from the group consisting of an anticoagulant protein, an antithrombotic protein, a clotting protein, a platelet protein, an anti-inflammatory protein, an antibody, an immunoglobulin, a defense protein, an enzyme, a hormone, a growth factor, a globular protein, a blood protein, a regulatory protein, a transport protein, a fibrous protein, a structural protein, a membrane protein, a cell attachment protein, a proteoglycan, a toxin, and a ligand.

44. The method of claim 42, wherein the glycoprotein is a naturally occurring glycoprotein.

45. The method of claim 42, wherein the glycoprotein is synthesized chemically.

46. The method of claim 42, wherein the glycopeptide is selected from the group consisting of an anticoagulant peptide, an antithrombotic peptide, a clotting peptide, a platelet peptide, an anti-inflammatory peptide, a defense peptide, an enzyme, a hormone, a growth factor, a neurotransmitter, a cytokine, a blood peptide, a regulatory peptide, a transport peptide, a fibrous peptide, a structural peptide, a membrane peptide, a cell attachment peptide, a toxin, an antibiotic, and a ligand.

47. The method of claim 42, wherein the glycopeptide is a naturally occurring glycopeptide.

48. The method of claim 42, wherein the glycopeptide is synthesized chemically.

49. The method of claim 39, wherein the periodate comprises at least one of periodic acid, sodium periodate, alkali metal periodates, and potassium periodate.

50. The method of claim 39, wherein the periodate is combined with 1,2 dihydroxy moiety and the amine moiety in an aqueous solution having a pH between about 4 and about 9.

51. The method of claim 39, wherein the periodate is combined with the 1,2 dihydroxy moiety and the amine moiety in an aqueous solution having a temperature between about 0 and about 50 degrees Celsius.

52. The method of claim 39, wherein the oxidizing step is performed in the absence of light.

53. The method of claim 39, wherein the reducing agent comprises at least one of sodium borohydride, sodium cyanoborohydride, and amine borane.

54. The method of claim 39, wherein the reducing agent is combined with the material comprising an imine moiety in an aqueous solution having a pH between about 6 and about 10.

55. The method of claim 39, wherein the reducing agent is combined with the imine moiety in an aqueous solution having a temperature between about 0 and about 50 degrees Celsius.

56. The method of claim 39, further comprising the step of combining the crosslinked biomaterial with a bioagent.

57. The method of claim 56, wherein the biomolecule is selected from the group consisting of an anticoagulant, an antithrombotic, an anti-inflammatory, an antibody, an immunoglobulin, an enzyme, a hormone, a growth factor, a neurotransmitter, a cytokine, a globular protein, a structural protein, a membrane protein, a cell attachment protein, a structural peptide, a membrane peptide, a cell attachment peptide, a proteoglycan, a toxin, an antibiotic, and a ligand.

58. The method of claim 39, wherein the crosslinked biomaterial is employed as a coating on a surface of the medical device, the coating imparting improved biocompatibility characteristics to the surface, the surface being suitable for contacting tissue, blood and other bodily fluids in or temporarily removed from a living mammalian subject.

59. The method of claim 58, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

60. The method of claim 58, wherein at least a portion of the surface forms at least one of a tube, a rod, a membrane, a balloon, a bag and a sheet.

61. The method of claim 58, wherein the surface comprises at least one of a biocompatible material selected from the group consisting of metal, titanium, titanium alloys, tin-nickel alloys, shape memory alloys, aluminum oxide, platinum, platinum alloys, stainless steel, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

62. The method of claim 58, comprising the further step of combining the coating with a bioagent.

63. The method of claim 62, wherein the bioagent is selected from the group consisting of an anticoagulant, an antithrombotic, an anti-inflammatory, an antibody, an immunoglobulin, an enzyme, a hormone, a growth factor, a neurotransmitter, a cytokine, a globular protein, a structural protein, a membrane protein, a cell attachment protein, a structural peptide, a membrane peptide, a cell attachment peptide, a proteoglycan, a toxin, an antibiotic, and a ligand.

* * * * *